(12) United States Patent
DeBruyne et al.

(10) Patent No.: US 9,855,129 B2
(45) Date of Patent: Jan. 2, 2018

(54) MULTI-LEVEL SUTURE ATTACHMENTS FOR COUPLING A STENT TO GRAFT MATERIAL

(71) Applicant: Cook Medical Technologies LLC, Bloomington, IN (US)

(72) Inventors: Michael P. DeBruyne, Bloomington, IN (US); Siddharth Vad, Bloomington, IN (US)

(73) Assignee: COOK MEDICAL TECHNOLOGIES LLC, Bloomington, IN (US)

(*) Notice: Subject to any disclaimer, the term of this patent is extended or adjusted under 35 U.S.C. 154(b) by 194 days.

(21) Appl. No.: 14/062,167

(22) Filed: Oct. 24, 2013

(65) Prior Publication Data

US 2014/0121757 A1    May 1, 2014

Related U.S. Application Data

(60) Provisional application No. 61/720,808, filed on Oct. 31, 2012.

(51) Int. Cl.
*A61F 2/07* (2013.01)
*A61F 2/95* (2013.01)
(Continued)

(52) U.S. Cl.
CPC .............. *A61F 2/07* (2013.01); *A61F 2/95* (2013.01); *A61F 2/848* (2013.01); *A61F 2002/075* (2013.01); *A61F 2002/8486* (2013.01); *A61F 2002/9511* (2013.01); *A61F 2002/9665* (2013.01); *A61F 2220/0016* (2013.01)

(58) Field of Classification Search
CPC ........ A61F 2002/075; A61F 2002/8486; A61F 2/848
See application file for complete search history.

(56) References Cited

U.S. PATENT DOCUMENTS

| 2003/0176912 A1* | 9/2003 | Chuter | ...................... A61F 2/07 623/1.13 |
| 2009/0204202 A1* | 8/2009 | Dierking | .................... A61F 2/91 623/1.16 |

FOREIGN PATENT DOCUMENTS

| WO | WO00/30562 | 6/2000 |
| WO | WO2009/145901 | 12/2009 |
| WO | WO 2009/145901 | * 12/2009 |

OTHER PUBLICATIONS

Examination Report for European Patent Application 13275274.2 issued Jan. 22, 2016, 5 pgs.
(Continued)

*Primary Examiner* — Corrine McDermott
*Assistant Examiner* — Joshua Levine
(74) *Attorney, Agent, or Firm* — Brinks Gilson & Lione (57) ABSTRACT

The present embodiments provide stent-grafts. In one embodiment, a stent has proximal and distal ends, a plurality of strut segments disposed between the proximal and distal ends that enable expansion of the stent from a compressed state to a deployed state, and a series of distal apices disposed at the distal end of the stent. At least a portion of a first distal apex overlaps with graft material. First and second sutures are each coupled between a portion of the first distal apex and the graft material. The first and second sutures are positioned at different longitudinal zones that lack an axial overlap with one another.

16 Claims, 4 Drawing Sheets

(51) Int. Cl.
  *A61F 2/966* (2013.01)
  *A61F 2/848* (2013.01)

(56) References Cited

OTHER PUBLICATIONS

Response to Extended European Search Report for 13275274.2 filed Nov. 24, 2014, 9 pgs.
Extended European Search Report for 13275274.2 dated Apr. 28, 2014, 7 pgs.
Intention to Grant European Patent Application 13275274.2 issued Oct. 11, 2016, 25 pgs.
Examination Report for European Patent Application 13 275 274.2 dated Mar. 7, 2017, 6 pgs.

* cited by examiner

MULTI-LEVEL SUTURE ATTACHMENTS FOR COUPLING A STENT TO GRAFT MATERIAL

PRIORITY CLAIM

This invention claims the benefit of priority of U.S. Provisional Application Ser. No. 61/720,808, entitled "Multi-Level Suture Attachments for Coupling a Stent to Graft Material," filed Oct. 31, 2012, the disclosure of which is hereby incorporated by reference in its entirety.

BACKGROUND

The present embodiments relate generally to apparatus and methods for treating medical conditions, and more specifically, to stent-grafts for use in body vessels to treat those medical conditions.

Stents may be inserted into an anatomical vessel or duct for various purposes. Stents may maintain or restore patency in a formerly blocked or constricted passageway, for example, following a balloon angioplasty procedure. Other stents may be used for different procedures, for example, stents placed in or about a graft have been used to hold the graft in an open configuration to treat an aneurysm. Additionally, stents coupled to one or both ends of a graft may extend proximally or distally away from the graft to engage a healthy portion of a vessel wall away from a diseased portion of an aneurysm to provide endovascular graft fixation.

Stents may be either self-expanding or balloon-expandable, or they can have characteristics of both types of stents. Self-expanding stents may be delivered to a target site in a compressed configuration and subsequently expanded by removing a delivery sheath, removing trigger wires and/or releasing diameter reducing ties. With self-expanding stents, the stents expand primarily based on their own expansive force without the need for further mechanical expansion. In a stent made of a shape-memory alloy such as nitinol, the shape-memory alloy may be employed to cause the stent to return to a predetermined configuration upon removal of the sheath or other device maintaining the stent in its predeployment configuration.

If stents are coupled to a graft, sutures are commonly threaded between a portion of the stent and the graft to provide a secure engagement. If multiple sutures are provided, safety may be increased in the event a suture breaks. However, the provision of multiple sutures can increase the overall amount of material used, which may arise in a larger profile when compressed in the delivery configuration. A larger delivery profile may reduce the overall number of patients who can be treated with such stent-grafts.

SUMMARY

The present embodiments provide stent-grafts. In one embodiment, a stent has proximal and distal ends, a plurality of strut segments disposed between the proximal and distal ends that enable expansion of the stent from a compressed state to a deployed state, and a series of distal apices disposed at the distal end of the stent. At least a portion of a first distal apex overlaps with graft material. First and second sutures are each coupled between a portion of the first distal apex and the graft material. The first and second sutures are positioned at different longitudinal zones that lack an axial overlap with one another.

In one example, a first suture bore is formed in the first distal apex, and the first suture is looped through at least the first suture bore and the graft material. Optionally, the second suture may be looped through the first suture bore and the graft material, in a manner such that the first and second sutures extend away from the first suture bore in different axial directions.

In other embodiments, a second suture bore may be formed in the first distal apex, and the second suture may be looped through at least the second suture bore and the graft material. The second suture further may be looped between the first and second suture bores. In various embodiments, an imaging bore may be positioned proximal to the first suture bore and distal to the second suture bore. The first suture bore and at least a portion of the imaging bore may overlap with the graft material, and the second suture bore may be disposed at least partially beyond a proximal edge of the graft material.

At least one barb may be integrally formed in a surface of the first distal apex at a location proximal to the imaging bore. The imaging bore may be disposed at the location corresponding to an endpoint of the proximal edge of the graft material.

In various embodiments, at least one suture extends around a proximal edge of the graft material to reduce the potential for infolding at the proximal edge.

Other systems, methods, features and advantages of the invention will be, or will become, apparent to one with skill in the art upon examination of the following figures and detailed description. It is intended that all such additional systems, methods, features and advantages be within the scope of the invention, and be encompassed by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like referenced numerals designate corresponding parts throughout the different views.

DETAILED DESCRIPTION OF THE
PREFERRED EMBODIMENTS

In the present application, the term "proximal" refers to a direction that is generally closest to the heart during a medical procedure, while the term "distal" refers to a direction that is furthest from the heart during a medical procedure.

Figure 1:
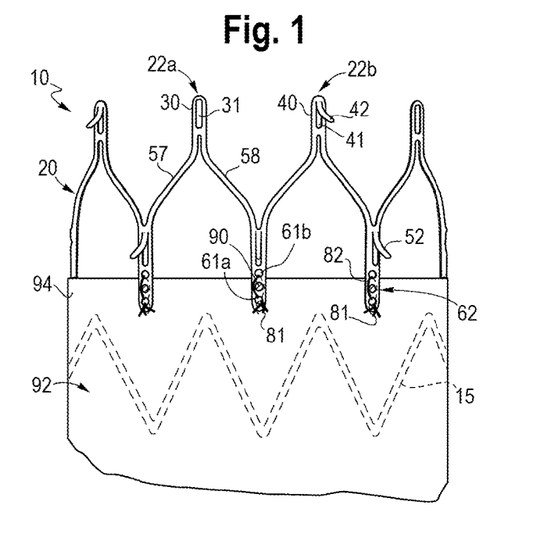
FIG. 1 is a side view of a portion of a stent-graft having a stent coupled to a proximal region of a graft material in accordance with a first embodiment.
Figure 2:
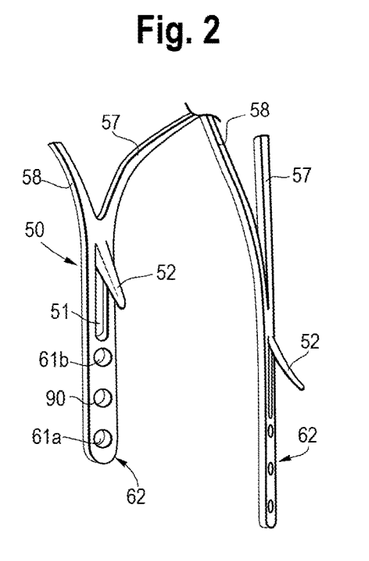
FIG. 2 is a perspective view of distal apices of the stent of FIG. 1.
Figure 3:
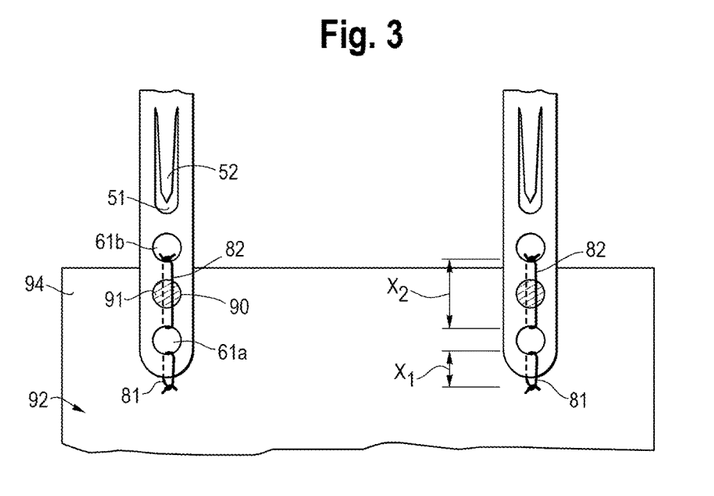
FIG. 3 is an enlarged side view of an interface between the distal apices of the stent and the proximal region of the graft material of FIG. 1.

Referring to FIGS. 1-3, a stent-graft 10 according to a first embodiment comprises a stent 20 and a graft material 92. In one non-limiting example, the stent 20 may be manufactured from a continuous cylinder into which a pattern may be cut by a laser or by chemical etching to produce slits in the wall of the cylinder. The resulting structure may then be heat set to give it a desired final configuration. In one exemplary final configuration, the proximal end of the stent 20 may comprise multiple adjacent proximal apices 22a and 22b, while the distal end of the stent 20 may comprise multiple adjacent distal apices 62, as shown in FIG. 1.

In one embodiment, at least one pair of adjacent, proximal apices 22a and 22b comprises different features. For example, as shown in FIG. 1, a first proximal apex 22a may comprise an end region 30 having a bore 31 formed therein, wherein the bore 31 is configured to receive a trigger wire. A second, adjacent proximal apex 22b comprises an end region 40 having an integral barb 42 formed therein, as shown in FIG. 1. However, the second proximal apex 22b is not configured to be restrained using a trigger wire. By using adjacent proximal apices 22a and 22b having the different features shown herein, an improved trigger wire attachment may be achieved and barb entanglement may be reduced, as explained further below.

The barbs 42 disposed in at least one of the end regions 40 of the second proximal apices 22b may be formed by laser cutting a desired barb shape into the end regions 40. A slit 41 therefore is formed into each end region 40 after the desired barb shape is formed, as shown in FIG. 1. Once the desired barb shape is cut, a main body of the barb 42 may be bent in a radially outward direction with respect to the end region 40. The angle may comprise any acute angle, or alternatively may be substantially orthogonal or obtuse. If desired, the barbs 42 may be sharpened, for example, by grinding the tip of the barb, to facilitate engagement at a target tissue site.

The proximal apices 22a and 22b of the stent 20 extend in a distal direction and form first and second angled strut segments 57 and 58, as shown in FIG. 1. A first strut segment 57 extending from a proximal apex 22a may meet with a second strut segment 58 extending from a proximal apex 22b to form a respective distal apex 62.

Expansion of the stent 20 is at least partly provided by the angled strut segments 57 and 58, which may be substantially parallel to one another in a compressed state, but may tend to bow outward away from one another in the expanded state shown in FIG. 1. In the expanded state, the first and second angled strut segments 57 and 58 may be disposed at an angle of about 20-60 degrees relative to the longitudinal axis of the stent 20, as depicted in FIG. 1.

The stent 20 has a reduced diameter delivery state so that it may be advanced to a target location within a vessel or duct. The stent 20 also has an expanded deployed state to apply a radially outward force upon at least a portion of a vessel or duct, e.g., to maintain patency within a passageway, or to hold open the lumen of a graft. In the expanded state, fluid flow is allowed through a central lumen of the stent 20. Further, the struts of the stent 20 may comprise a substantially flat wire profile or may comprise a rounded profile. As best seen in FIG. 2, the struts of the stent 20 generally comprise a flat wire profile.

The stent 20 may be manufactured from a super-elastic material. Solely by way of example, the super-elastic material may comprise a shape-memory alloy, such as a nickel titanium alloy (nitinol). If the stent 20 comprises a self-expanding material such as nitinol, the stent may be heat-set into the desired expanded state, whereby the stent 20 can assume a relaxed configuration in which it assumes the preconfigured first expanded inner diameter upon application of a certain cold or hot medium. Alternatively, the stent 20 may be made from other metals and alloys that allow the stent 20 to return to its original, expanded configuration upon deployment, without inducing a permanent strain on the material due to compression. Solely by way of example, the stent 20 may comprise other materials such as stainless steel, cobalt-chrome alloys, amorphous metals, tantalum, platinum, gold and titanium. The stent 20 also may be made from non-metallic materials, such as thermoplastics and other polymers.

The stent 20 may be delivered to a target site in a compressed configuration using a plurality of trigger wires. A single trigger wire may be looped through the bore 31 of selected ones of the first proximal apices 22a to restrain the stent 20 during delivery. Trigger wires are not coupled to the second proximal apices 22b, which comprise the barbs 42. Accordingly, the trigger wires are only disposed through alternating proximal apices 22a. By restraining selected ones of the first proximal apices, such as each first proximal apex 22a, the adjacent second proximal apices 22b also may be indirectly pulled in a radially inward direction during delivery. Advantageously, the overall number of trigger wires used may be reduced in this manner.

Each of distal apices 62 may be coupled to the graft material 92, for example, using one or more sutures that are looped through the graft material 92 and bores of the stent 20, as described further below. In this manner, the stent 20 may be used as an attachment stent for endovascular graft fixation. For example, the graft material 92 may overlap with an aneurysm to seal off fluid flow into the aneurysm, while the proximal end of the stent 20 may extend in a proximal direction away from the graft material 92, e.g., to engage a healthy portion of a vessel wall away from a diseased portion of the aneurysm.

In the embodiment of FIGS. 1-3, each of the distal apices 62 comprises first and second suture bores 61a and 61b that are adapted to receive a suture for coupling the distal end of the stent 20 to the graft material 92. Each of the distal apices 62 may also comprise an imaging bore 90 adapted to receive a suitable radiopaque marker 91, such as a gold marker. The imaging bore 90 may be beveled, or alternatively, may be substantially orthogonal to the strut of the distal apex 62. It is noted that FIG. 2 shows an imaging bore 90 where a marker has yet to be placed therein, while FIG. 3 shows the imaging bore 90 with the marker 91 secured therein.

In use, the imaging bores 90 may be aligned with the proximal edge 94 of the graft material 92 for example, when the stent 20 is used for endovascular graft fixation. More specifically, at least the first suture bore 61a overlaps with a proximal region of the graft material 92, thereby allowing a suture to couple the stent 20 to the graft material 92 with some desired degree of overlap. The proximal edge 94 of the graft material 92 therefore may be aligned with the imaging bores 90. Advantageously, a physician may know exactly where the proximal edge 94 of the graft material 92 is being placed because he or she can view the position of the radiopaque markers in the imaging bores 90. Therefore, the chances of inadvertently overlapping the graft material 92 with a branch vessel, or another undesired location, may be reduced.

Further, one or more of the distal apices 62 of the stent 20 may comprise at least one barb 52. In the embodiments of FIGS. 1-2, the at least one barb 52 is disposed proximal to each of the first and second suture bores 61a and 61b, and also proximal to the imaging bore 90. The at least one barb 52 may be formed integrally with its respective distal apex 62, e.g., by forming a slit 51 in the distal apex in the manner described above for the barbs 42, or alternately may comprise a barb that is externally secured to the distal apex 90.

In this example, the imaging bore 90 is disposed between the first and second suture bores 61a and 61b, as shown in FIGS. 1-3. While the imaging bore 90 is shown as being aligned just distal to a proximal end 94 of the graft material 92 in FIG. 3, the imaging bore 90 alternatively may be aligned precisely with the proximal end 94 of the graft material 92.

In various embodiments, the first suture bore 61a and at least a portion of the imaging bore 90 overlap with the graft material 92, and the second suture bore 61b is disposed at least partially beyond the proximal edge 94 of the graft material 92. The at least one barb 52 may be formed in a surface of the distal apex 62 at a location proximal to each of the imaging bore 90 and the first and second suture bores 61a and 61b. In the instance in which the at least one barb 52 is provided, it may be disposed proximally beyond the proximal edge 94 of the graft material 92.

The stent-graft 10 of FIGS. 1-3 further comprises at least first and second sutures 81 and 82. In one exemplary coupling, the first suture 81 is looped between the first suture bore 61a and the graft material 92, while the second suture 82 is looped between the first and second suture bores 61a and 62b and trough the graft material 92, as best seen in FIG. 3. The second suture 82 may extend longitudinally over the imaging bore 90 as it extends between the first and second suture bores 61a and 62, in the instance in which the imaging bore 90 is positioned between the first and second suture bores 61a and 62. The first and second sutures 81 and 82 may be threaded through the graft material 92 and securely knotted.

Advantageously, the embodiment of FIGS. 1-3 provides at least two different sutures 81 and 82 that are coupled between a single distal apex 62 of the stent 20 and the graft material 92. In the event that one of the sutures 81 or 82 coupled to a single distal apex breaks, there will still be at least one other suture coupled between that particular distal apex and the graft material 92.

As a further advantage, the sutures 81 and 82 preferably are positioned at different longitudinal zones that lack an overlap with one another, thereby reducing the amount of suture material at any given longitudinal location, which may significantly reduce the delivery profile. In particular, the first suture 81 may be positioned through the first suture bore 61a and extend distally therefrom in a manner that spans an axial length $x_1$, while the second suture 82 may be positioned through the first suture bore 61a and extend proximally therefrom towards the second suture bore 61b in a manner that spans an axial length $x_2$, as shown in FIG. 3.

Therefore the first and second sutures 81 and 82 are not longitudinally overlapping with one another along the axial zones $x_1$ and $x_2$. By positioning the sutures at different longitudinal levels, and thereby reducing the amount of suture material at any given longitudinal location to significantly reduce the delivery profile, the stent-graft 10 may be suitable for delivery in a larger portion of the population, including those with relatively small vessels, via smaller delivery systems.

Furthermore, since knots of the suture loop can add undesirable bulk to the delivery profile of the stent-graft 10, the knots of the first and second sutures 81 and 82 will not overlap with one another, since the first and second sutures 81 and 82 themselves are not longitudinally overlapping with one another along the axial zones $x_1$ and $x_2$. If desired, the knot of the first suture 81 may be positioned in a distal direction, while the knot of the second suture 82 may be positioned in a proximal direction, as depicted in FIG. 3, thereby further ensuring that these relatively bulky parts are not overlapping with one another. Moreover, the knot of the second suture 82 may be disposed proximally beyond the proximal edge 94 of the graft material 92, as shown in FIG. 3, thereby further reducing the delivery profile by not having the suture knot overlap with the graft material 92.

As yet a further advantage, by providing at least one suture attachment at the proximal edge 94 of the graft material 92, infolding at the proximal edge 94 may be significantly reduced. In particular, in the embodiment of FIGS. 1-3, at least the second sutures 82 is disposed around a portion of the proximal edge 94 of the graft material 92, thereby preventing infolding of the graft material 92 at this location and surrounding areas.

The stent-graft 10 of FIGS. 1-3 may comprise one or more stents 15 that are disposed circumferentially around an inner or outer surface of the graft material 92, or sandwiched between two different layers of graft material. While one exemplary Z-stent 15 is shown in FIG. 1, it will be apparent that any number of stents and stent shapes may be coupled to the graft material 92 to form the stent-graft 10. Moreover, while the Z-stent 15 shown in FIG. 1 is shown having proximal apices that positioned between adjacent distal apices 62 of the stent 20, the proximal apices of the Z-stent 15 alternatively may be aligned with the distal apices 62 of the stent 20.

Figure 4:
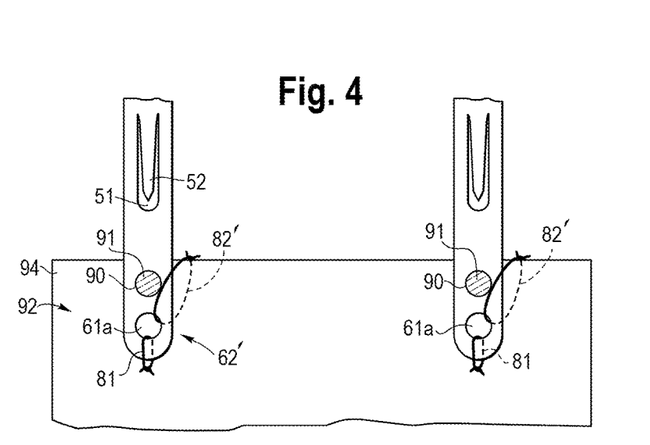
FIG. 4 is a side view of an alternative interface between distal apices of a stent and a proximal region of a graft material.

Referring now to FIGS. 4-10, various alternative embodiments of the interface between distal apices and graft material are shown and described, including alternative distal apex designs and/or suture attachments to the graft. The embodiment of FIG. 4 is similar to the embodiment of FIGS. 1-3, with like reference numerals representing corresponding parts, with a main exception that one or more alternative distal apices 62' comprises the first suture bore 61a, but the second suture bore 61b is omitted. Further, a modified second suture 82' is coupled between the first suture bore 61a and the proximal edge 94 of the graft material 92, as shown in FIG. 4. The second suture 82' thus extends, in an angled manner, through the distal apex 62 at a distal location and laterally around a side of the distal apex 62 at a proximal location. The embodiment of FIG. 4 encompasses several advantages of the embodiment of FIGS. 1-3, including but not limited to the provision of at least two different sutures that are coupled between a single distal apex of the stent 20 and the graft material 92 for added safety in the event that one suture breaks, the positioning of at least two sutures at different longitudinal zones that lack an overlap with one another to reduce the amount of suture material at any given longitudinal location and reduce the delivery profile, the longitudinal offset of positioning of knots of different sutures, and the provision of at least one suture attachment at the proximal edge 94 of the graft material 92 to reduce the potential for infolding at the proximal edge 94.

Figure 5:
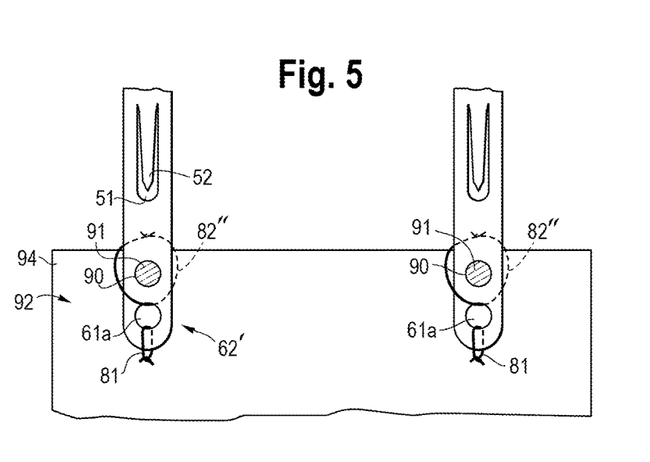
FIG. 5 is a side view of a further alternative interface between distal apices of a stent and a proximal region of a graft material.

Referring to FIG. 5, this alternative embodiment is similar to the embodiment of FIG. 4, with a main exception that while the modified second suture 82' of FIG. 4 extends to the side of the distal apex 62', in the embodiment of FIG. 5 a modified second suture 82" is coupled between the first suture bore 61a and the proximal edge 94 of the graft material 92 and spans at least 360 degrees around the perimeter or width of the distal apex 62'. The embodiment of FIG. 5 encompasses at least the multiple advantages of the embodiments of FIGS. 1-3 and FIG. 4, as explained above.

Figure 6:
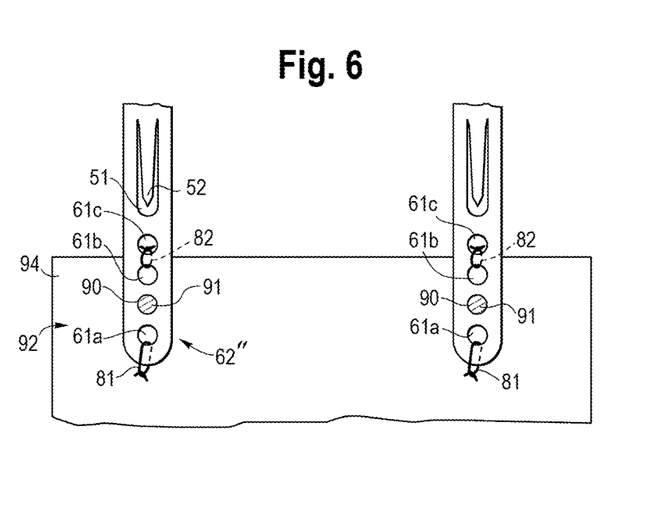
FIG. 6 is a side view of yet a further alternative interface between distal apices of a stent and a proximal region of a graft material.

Referring to FIG. 6, this alternative embodiment is similar to the embodiment of FIGS. 1-3, with a main exception that a third suture bore 61c is provided. In this example, the first and second suture bores 61a and 61b, and the imaging bore 90, are each disposed distal to the proximal edge 94 of the graft material 92, while the third suture bore 61c is disposed at least partially beyond the proximal edge 94. Further, the second suture 82 is disposed between the second suture bore 61b and the third suture bore 61c. The embodiment of FIG. 6 encompasses at least the multiple advantages of the embodiments of FIGS. 1-3, FIG. 4 and FIG. 5, as explained above.

Figure 7:
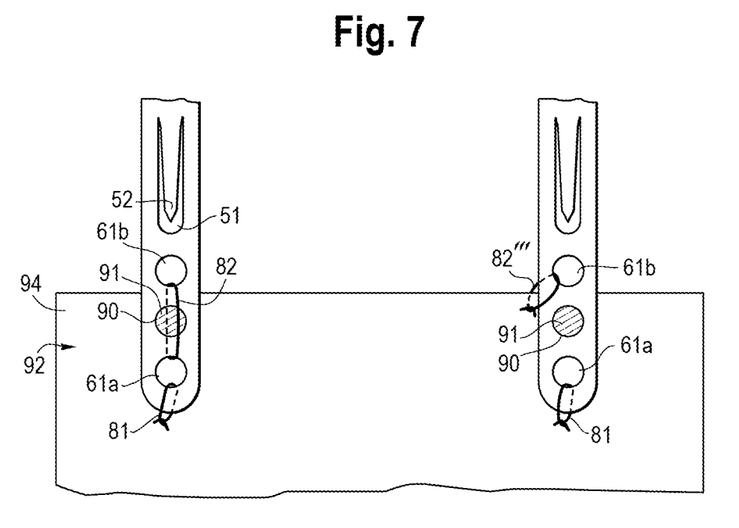
FIG. 7 is a side view of yet a further alternative interface between distal apices of a stent and a proximal region of a graft material.

Referring to FIG. 7, this alternative embodiment is similar to the embodiment of FIGS. 1-3, with a main exception that at least one alternative second suture 82''' is coupled between the second suture bore 61b and the graft material 92. The embodiment of FIG. 7 encompasses at least the multiple advantages of the embodiments of FIGS. 1-6, as explained above.

Figure 8:
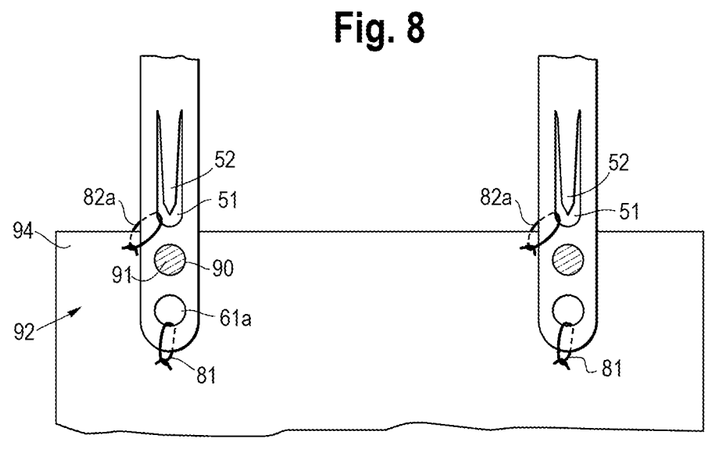
FIG. 8 is a side view of yet a further alternative interface between distal apices of a stent and a proximal region of a graft material.

Referring to FIG. 8, this alternative embodiment is similar to the embodiment of FIGS. 4-5, with a main exception that at least one alternative second suture 82a is coupled between the open space of the slit 51 of the distal apex and the graft material 92. In this example, the slit 51 may be positioned closer to the proximal edge 94 of the graft material 92 to yield a shorter distance that the second suture 82a spans, although the barb 52 is still disposed proximal to the proximal edge 94 of the graft material 92, as shown in FIG. 8. The embodiment of FIG. 8 encompasses at least the multiple advantages of the embodiments of FIGS. 1-7, as explained above.

Figure 9:
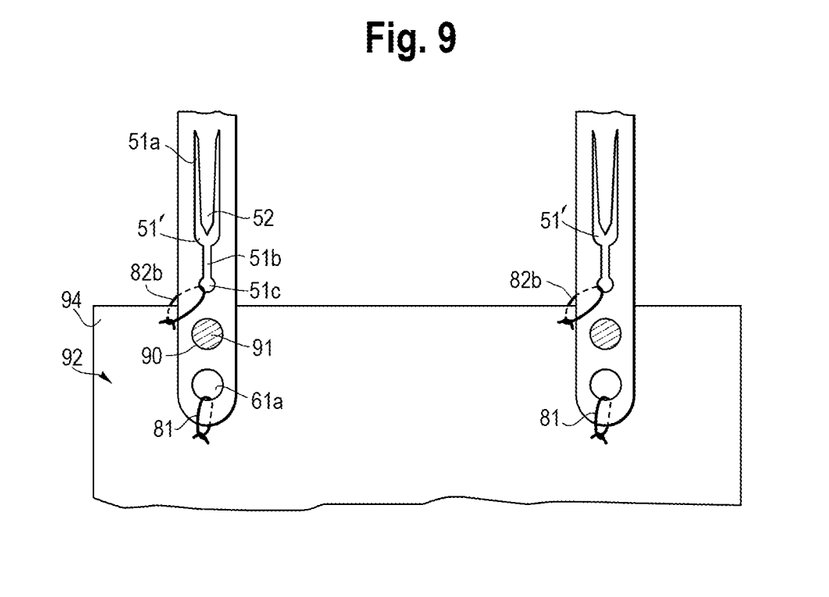
FIG. 9 is a side view of yet a further alternative interface between distal apices of a stent and a proximal region of a graft material.

Referring to FIG. 9, this alternative embodiment is similar to the embodiment of FIGS. 4-5, with a main exception that at least one alternative slit 51' of the distal apex comprises a main width 51a, a reduced width 51b, and a coupling zone 51c for receiving a portion of a second suture 82b, which is looped through the coupling zone 51c and the graft material 92. The coupling zone 51c may comprise a width that is larger than the reduced width 51b, thereby ensuring that the second suture 82b stays within the coupling zone 51c and does not move proximally up the slit 51'. The coupling zone 51c may be positioned slightly proximal to the proximal edge 94 of the graft material 92, as shown in FIG. 9. The embodiment of FIG. 9 encompasses at least the multiple advantages of the embodiments of FIGS. 1-8, as explained above.

Figure 10:
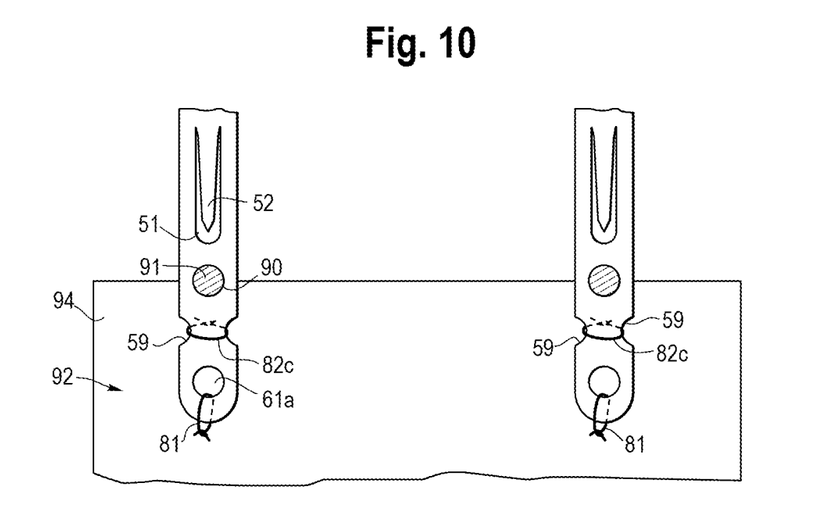
FIG. 10 is a side view of yet a further alternative interface between distal apices of a stent and a proximal region of a graft material.

Referring to FIG. 10, this alternative embodiment is similar to the embodiment of FIGS. 4-5, with a main exception that at least one alternative distal apex comprises a notched region 59 for receiving a second suture 82c. The notched region 59 may comprise a width that is less than a main width of the distal apex, thereby ensuring that the second suture 82c stays within the notched region 59 and does not move longitudinally. In this exemplary depiction, the imaging bore 90 is aligned precisely at the proximal end of the graft material 92, and the notched region 59 is positioned between the imaging bore 90 and the first suture bore 61a, as shown in FIG. 10. The embodiment of FIG. 10 encompasses at least the multiple advantages of the embodiments of FIGS. 1-9, as explained above.

Moreover, it will be appreciated that while between one and three suture bores are shown in the embodiments of FIGS. 1-10, additional suture bores may be provided on any particular distal apex of the stent.

While various embodiments of the invention have been described, the invention is not to be restricted except in light of the attached claims and their equivalents. Moreover, the advantages described herein are not necessarily the only advantages of the invention and it is not necessarily expected that every embodiment of the invention will achieve all of the advantages described.

We claim:

1. A stent-graft, comprising:
a stent having proximal and distal ends, a plurality of strut segments disposed between the proximal and distal ends that enable expansion of the stent from a compressed state to a deployed state, and a series of distal apices disposed at the distal end of the stent;
graft material coupled to the stent, where at least a portion of a first distal apex of the stent overlaps with the graft material;
first and second sutures that are each coupled between a portion of the first distal apex and the graft material;
a first suture bore formed in the first distal apex, wherein the first suture is looped through at least the first suture bore and the graft material;
a second suture bore formed in the first distal apex, wherein the second suture is looped through at least the second suture bore and the graft material; and
where the second suture is positioned entirely proximal relative to the first suture.

2. The stent-graft of claim 1 where the second suture is looped through the first suture bore and the graft material, where the first and second sutures extend away from the first suture bore in different axial directions.

3. The stent-graft of claim 1, where the second suture further is looped between the first and second suture bores.

4. The stent-graft of claim 1 further comprising an imaging bore formed in the first distal apex.

5. The stent-graft of claim 4, where the imaging bore is positioned proximal to the first suture bore and distal to a second suture bore.

6. The stent-graft of claim 5, where the first suture bore and at least a portion of the imaging bore overlap with the graft material, and the second suture bore is disposed at least partially beyond a proximal edge of the graft material.

7. The stent-graft of claim 1 further comprising at least one barb integrally formed in a surface of the first distal apex.

8. A stent-graft, comprising:
a stent having proximal and distal ends, a plurality of strut segments disposed between the proximal and distal ends that enable expansion of the stent from a compressed state to a deployed state, and a series of distal apices disposed at the distal end of the stent;
graft material coupled to the stent, where at least a portion of a first distal apex overlaps with the graft material;
an imaging bore formed in the first distal apex;

a first suture bore formed in the first distal apex;
a second suture bore formed in the first distal apex;
a first suture looped through at least the first suture bore and the graft material; and
a second suture looped through at least the second suture bore and the graft material,
where the second suture is positioned entirely proximal relative to the first suture.

9. The stent-graft of claim 8 where the second suture further is looped between the first and second suture bores.

10. The stent-graft of claim 8 where the imaging bore is positioned proximal to the first suture bore and distal to the second suture bore.

11. The stent-graft of claim 10 where the first suture bore and at least a portion of the imaging bore overlap with the graft material, and the second suture bore is disposed at least partially beyond a proximal edge of the graft material.

12. The stent-graft of claim 8 further comprising at least one barb integrally formed in a surface of the first distal apex at a location proximal to the imaging bore and the suture bore.

13. The stent-graft of claim 12 where the at least one barb is disposed proximally beyond the graft material.

14. A stent-graft, comprising:
a stent having proximal and distal ends, a plurality of strut segments disposed between the proximal and distal ends that enable expansion of the stent from a compressed state to a deployed state, and a series of distal apices disposed at the distal end of the stent;
graft material coupled to the stent, where at least a portion of a first distal apex overlaps with the graft material;
a first suture bore formed in the first distal apex; and
first suture and second sutures disposed through the first suture bore for coupling a portion of the first distal apex to the graft material,
here the second suture extends proximally beyond a proximal edge of the graft material to reduce the potential for infolding at the proximal edge.

15. The stent-graft of claim 14 further comprising an imaging bore formed in the first distal apex, wherein the imaging bore is positioned proximal to the at least one suture bore.

16. The stent-graft of claim 14 further comprising:
the first suture looped through at least a first suture bore and the graft material; and
the second suture looped through at least a second suture bore and the graft material.

* * * * *